(12) United States Patent
Shao et al.

(10) Patent No.: US 12,153,035 B2
(45) Date of Patent: Nov. 26, 2024

(54) METHODS AND INTERNET OF THINGS SYSTEMS FOR VISUAL MANAGEMENT OF SMART GAS DATA CENTER PROCESSES

(71) Applicant: CHENGDU QINCHUAN IOT TECHNOLOGY CO., LTD., Sichuan (CN)

(72) Inventors: Zehua Shao, Chengdu (CN); Yong Li, Chengdu (CN); Junyan Zhou, Chengdu (CN); Yuefei Wu, Chengdu (CN)

(73) Assignee: CHENGDU QINCHUAN IOT TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 18/586,413

(22) Filed: Feb. 23, 2024

(65) Prior Publication Data

US 2024/0201156 A1 Jun. 20, 2024

(30) Foreign Application Priority Data

Sep. 13, 2023 (CN) .......................... 202311175809.3

(51) Int. Cl.
*G01N 33/00* (2006.01)
*G06F 16/901* (2019.01)

(52) U.S. Cl.
CPC ..... *G01N 33/0063* (2013.01); *G01N 33/0034* (2013.01); *G06F 16/9024* (2019.01)

(58) Field of Classification Search
CPC ............ G01N 33/0063; G01N 33/0034; G06F 16/9024

(Continued)

(56) References Cited

U.S. PATENT DOCUMENTS

| 8,838,390 B1* | 9/2014 | Selman ................... E21B 47/00 |
| | | 702/9 |
| 2016/0010445 A1* | 1/2016 | Harrison ................. E21B 47/00 |
| | | 702/6 |

(Continued)

FOREIGN PATENT DOCUMENTS

| CN | 103345400 B | 8/2016 |
| CN | 107943668 A | 4/2018 |

(Continued)

OTHER PUBLICATIONS

First Office Action in Chinese Application No. 202311175809.3 mailed on Oct. 25, 2023, 13 pages.

(Continued)

*Primary Examiner* — Kerri L McNally
(74) *Attorney, Agent, or Firm* — METIS IP LLC (57) ABSTRACT

The embodiment of the present disclosure provides methods and Internet of Things systems for visual management of smart gas data center processes. The method is executed by a smart gas management platform of the Internet of Things system. The method includes: obtaining a data acquisition feature and first sampling data; obtaining a data summary feature and second sampling data; obtaining a first task list and a second task list, determining a first processing feature of the first task list and a second processing feature and a queuing feature of the second task list; determining an estimation feature, the estimation feature at least including an estimated completion time of the at least one gas task, and an estimated queuing time of the at least one pending gas task; generating first visualization data; and controlling at least one target platform to display the first visualization data.

3 Claims, 5 Drawing Sheets

(58) Field of Classification Search
USPC .......................................................... 340/632
See application file for complete search history.

(56) References Cited

U.S. PATENT DOCUMENTS

| | | | |
|---|---|---|---|
| 2016/0356666 A1* | 12/2016 | Bilal | G01M 3/2807 |
| 2017/0102693 A1* | 4/2017 | Kidd | G05B 19/41865 |
| 2017/0102694 A1 | 4/2017 | Enver et al. | |
| 2019/0138995 A1 | 5/2019 | Currin et al. | |
| 2020/0012634 A1* | 1/2020 | Eberhardt | G01M 99/00 |
| 2022/0398665 A1* | 12/2022 | Jayathirtha | G06Q 40/06 |
| 2023/0196242 A1* | 6/2023 | Kumar | G06F 16/9024 |
| | | | 705/7.27 |

FOREIGN PATENT DOCUMENTS

| | | |
|---|---|---|
| CN | 111324460 A | 6/2020 |
| CN | 112241924 A | 1/2021 |
| CN | 114019891 A | 2/2022 |
| CN | 115129957 A | 9/2022 |
| CN | 116226116 A | 6/2023 |
| CN | 116503975 A | 7/2023 |
| CN | 116539128 A | 8/2023 |
| KR | 20200074825 A | 6/2020 |

OTHER PUBLICATIONS

Decision to grant a patent in Chinese Application No. 202311175809.3 mailed on Nov. 10, 2023, 4 pages.
Qiao, Wukang et al., Construction of a Smart Gas System based on the Internet of Everything, Innovation World Weekly, 2019, 9 pages.
Shao, Zehua, Research on Intelligent Gas Meter Cloud Platform, Gas & Heat, 38(3): 30-34, 2018.
Macker A. et al., ARDUINO Based LPG Gas Monitoring & Automatic Cylinder Booking with Alert System, 2018 2nd International Conference on Trends in Electronics and Informatics (ICOEI), 2019, 4 pages.

* cited by examiner

METHODS AND INTERNET OF THINGS SYSTEMS FOR VISUAL MANAGEMENT OF SMART GAS DATA CENTER PROCESSES

CROSS-REFERENCE TO RELATED APPLICATION

This application claims priority of Chinese Patent Application No. 202311175809.3, filed on Sep. 13, 2023, the entire contents of which are incorporated herein by reference.

TECHNICAL FIELD

The present disclosure relates to the field of data visualization, and in particular, to a method and an Internet of Things (IOT) system for visual management of smart gas data center processes.

BACKGROUND

As the gas industry enters the era of big data, a large amount of gas data needs to be processed in the operation and management process of gas pipeline networks. Due to the wide range of sources of gas data, issues in the data source itself, network transmission, and data processing processes will affect the quality of data processing. It is necessary to visually present the process of analyzing and processing gas data to provide early warnings in case of abnormalities during the data processing process.

CN103345400B proposes a method and a device for data processing, which allows for monitoring gas data in a visual form by providing a visual computing component based on injected data. However, it does not address how to provide visual warnings in case of abnormalities occurring in various gas data processes.

Thereby, a method and an Internet of Things system for visual management of smart gas data center processes are provided, which enables real-time monitoring of gas data processing and analysis processes while displaying abnormal data when anomalies occur to facilitate timely visual warnings.

SUMMARY

One or more embodiments of the present disclosure provide a method for visual management of smart gas data center processes, the method is executed by a smart gas management platform of an Internet of Things system for visual management of smart gas data center processes, comprising: obtaining a data acquisition feature and first sampling data; obtaining a data summary feature and second sampling data; obtaining a first task list and a second task list, determining a first processing feature of the first task list and a second processing feature and a queuing feature of the second task list; wherein the first task list includes at least one gas task, and the second task list includes at least one pending gas task; determining an estimation feature based on the data acquisition feature, the data summary feature, the first processing feature, the second processing feature, and the queuing feature, the estimation feature at least including an estimated completion time of the at least one gas task, and an estimated queuing time of the at least one pending gas task; generating first visualization data according to the first sampling data, the second sampling data, and the estimation feature; and controlling at least one target platform to display the first visualization data.

One or more embodiments of the present disclosure provide an Internet of Things system for visual management of smart gas data center processes, the Internet of Things system includes a smart gas management platform, the smart gas management platform includes a smart gas data center, and the smart gas management platform is configured to: obtain a data acquisition feature and first sampling data; obtain a data summary feature and second sampling data; obtain a first task list and a second task list, determine a first processing feature of the first task list; and a second processing feature and a queuing feature of the second task list; the first task list includes at least one gas task, and the second task list includes at least one pending gas task; determine an estimation feature based on the data acquisition feature, the data summary feature, the first processing feature, the second processing feature, and the queuing feature, the estimation feature at least including an estimated completion time of the at least one gas task, and an estimated queuing time of the at least one pending gas task; generate first visualization data according to the first sampling data, the second sampling data, and the estimation feature; and control at least one target platform to display the first visualization data.

One or more embodiments of the present disclosure provide a non-transitory computer-readable storage medium storing computer instructions, wherein when reading the computer instructions, a computer executes the method for visual management of smart gas data center processes.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. Obviously, drawings described below are only some examples or embodiments of the present disclosure. Those skilled in the art, without further creative efforts, may apply the present disclosure to other similar scenarios according to these drawings. It should be understood that the purposes of these illustrated embodiments are only provided to those skilled in the art to practice the application, and not intended to limit the scope of the present disclosure. Unless obviously obtained from the context or the context illustrates otherwise, the same numeral in the drawings refers to the same structure or operation.

It will be understood that the terms "system," "device," "unit," and/or "module" used herein are one method to distinguish different components, elements, parts, sections, or assemblies of different levels in ascending order. However, the terms may be displaced by other expressions if they may achieve the same purpose.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The flowcharts used in the present disclosure illustrate operations that systems implement according to some embodiments of the present disclosure. It is to be expressly understood, the operations of the flowcharts may be implemented not in order. Conversely, the operations may be implemented in an inverted order, or simultaneously. Moreover, one or more other operations may be added to the flowcharts. One or more operations may be removed from the flowcharts.

Due to the wide range of sources of gas data, and the fact that the gas data processing process is realized between different modules of various gas platforms, any issues with the data source itself, network transmission, or data processing process can impact the quality of data processing. It is necessary to visualize and manage the process of gas data analysis and processing to provide visual early warnings when abnormalities occur in the data processing flow. While existing technologies offer methods to monitor gas data using visualization, they do not address how to issue visual warnings when abnormalities occur in each stage of gas data processing. Therefore, in some embodiments of the present disclosure, by obtaining a data acquisition feature, a data summary feature, first sampling data, and second sampling data from a smart gas data center, abnormal data and its corresponding probability are determined. Based on an estimated feature, a warning mark can be established, enabling the visualization of data from the smart gas IoT platform and the status of gas task execution. Visual warnings can be issued in case of anomalies in the gas process or data processing exceeding the time limit.

Figure 1:
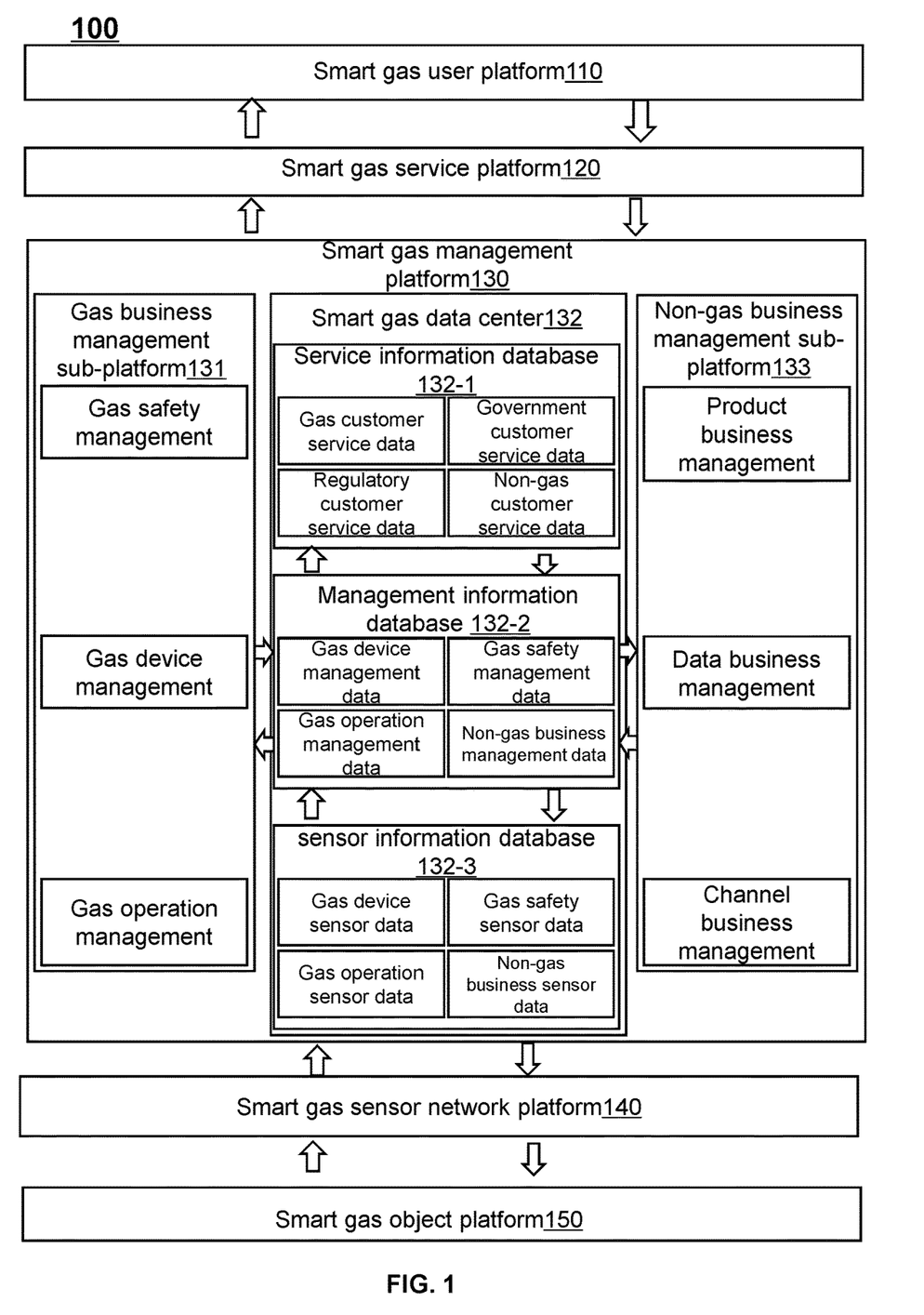
FIG. 1 is an exemplary schematic diagram of an Internet of Things system for visual management of smart gas data center processes according to some embodiments of the present disclosure.

FIG. 1 is an exemplary schematic diagram of an Internet of Things system 100 for visual management of smart gas data center processes according to some embodiments of the present disclosure.

As shown in FIG. 1, the IoT system 100 may include a smart gas user platform 110, a smart gas service platform 120, a smart gas management platform 130, a smart gas sensor network platform 140, and a smart gas object platform 150.

The smart gas user platform 110 may be a platform for interacting with the user. In some embodiments, the smart gas user platform 110 may be configured as a terminal device.

The smart gas service platform 120 may be a platform for communicating the user's demand and control information. For example, the smart gas service platform 120 may obtain gas information from the smart gas management platform 130 and send it to the smart gas user platform 110.

The smart gas management platform 130 may be a platform that coordinates and harmonizes the connection and collaboration between various functional platforms, and aggregates all the information of the IoT to provide perception management and control management functions for the IoT operation system. In some embodiments, the smart gas management platform 130 may include a gas business management sub-platform 131, a smart gas data center 132, and a non-gas business management sub-platform 133.

The gas business management sub-platform 131 may be a platform for managing gas business. In some embodiments, the gas business management sub-platform 131 may be used for performing gas safety management, gas device management, and gas operation management.

The non-gas business management sub-platform 133 may be a platform for managing non-gas business. In some embodiments, the non-gas business management sub-platform 133 may be used for performing product business management, data business management, and channel business management.

The smart gas data center 132 may be used to store and manage all operational information of the IoT system 100. In some embodiments, the smart gas data center 132 may be configured as a storage device for storing data related to gas information, etc.

In some embodiments, the smart gas data center 132 may include a service information database 132-1, a management information database 132-2, and a sensor information database 132-3. The service information database 132-1 is used to store service information data, including gas user service data, government user service data, regulatory user service data, and non-gas user service data. The management information database 132-2 is used to store management information data, including gas device management data, gas safety management data, gas operation management data, and non-gas business management data. The sensor information database 132-3 is used to store sensor information data, including gas device sensor data, gas safety sensor data, gas operation sensor data, and non-gas business sensor data. In some embodiments, the smart gas data center 132 may obtain visual data of the data storage situation of the smart gas management platform, such as the data storage load situation of the databases, the sub-platforms, or the like.

The management information database 132-2 bi-directionally interacts with the sensor information database 132-3 and the service information database 132-1, respectively, and the sensor information database 132-3 performs the information interaction with the smart gas sensor network platform 140, and the service information database 132-1 interacts with the smart gas service platform 120. The gas service management sub-platform 131 and the non-gas business management sub-platform 133 interact information-wise with the management information database 132-2, obtain corresponding management data from the management information database 132-2, and send management instructions to the management information database 132-2, which is further sent by the management information database 132-2 to the service information database 132-1 or the sensor information database 132-3 according to the needs of the instructions to realize the external transmission of information.

In some embodiments, the smart gas management platform 130 may interact with the smart gas service platform 120 and the smart gas sensor network platform 140, respectively, through the smart gas data center 132. For example, the smart gas data center 132 may send gas data transmission information to the smart gas service platform. As another example, the smart gas data center may send an instruction to obtain gas data transmission information to the smart gas sensor network platform 140 to obtain the gas data transmission information.

In some embodiments, the smart gas management platform 130 (e.g., the smart gas data center 132) may be used for obtaining a data acquisition feature and first sampling data; obtaining a data summary feature and second sampling data; obtaining a first task list and a second task list, determining a first processing feature of the first task list, and determining a second processing feature and a queuing feature of the second task list; determining an estimation feature based on the data acquisition feature, the data summary feature, the first processing feature, the second processing feature, and the queuing feature; generating first visualization data based on the first sampling data, the second sampling data, and the estimation feature; and sending the first visualization data to at least one of the smart gas user platform, the smart gas service platform, the smart gas sensor network platform, and the smart gas object platform, and controlling the at least one target platform to display the first visualization data.

The smart gas sensor network platform 140 may be a functional platform that manages sensor communications. In some embodiments, the smart gas sensor network platform 140 may be configured as a communication network and gateway. In some embodiments, the smart gas data center 132 may obtain data transmission of the smart gas sensor network platform 140, e.g., data loads at different time periods of different sensor network sub-platforms, etc.

The smart gas object platform 150 may be a functional platform for sensor information generation and controlling information execution. In some embodiments, the smart gas object platform 150 may be configured as various types of gas device and monitoring devices. In some embodiments, the smart gas data center 132 may obtain monitoring data of a plurality of devices of the smart gas object platform 150, e.g., operating status and frequency of uploading data of each device, or the like.

In some embodiments of the present disclosure, based on the IoT system 100, an information operation closed loop can be formed between the smart gas object platform 150 and the smart gas user platform 110, and coordinated and regular operation can be carried out under the unified management of the smart gas management platform 130, so as to realize the visualization and intelligence of the gas data and the gas tasks.

Figure 2:
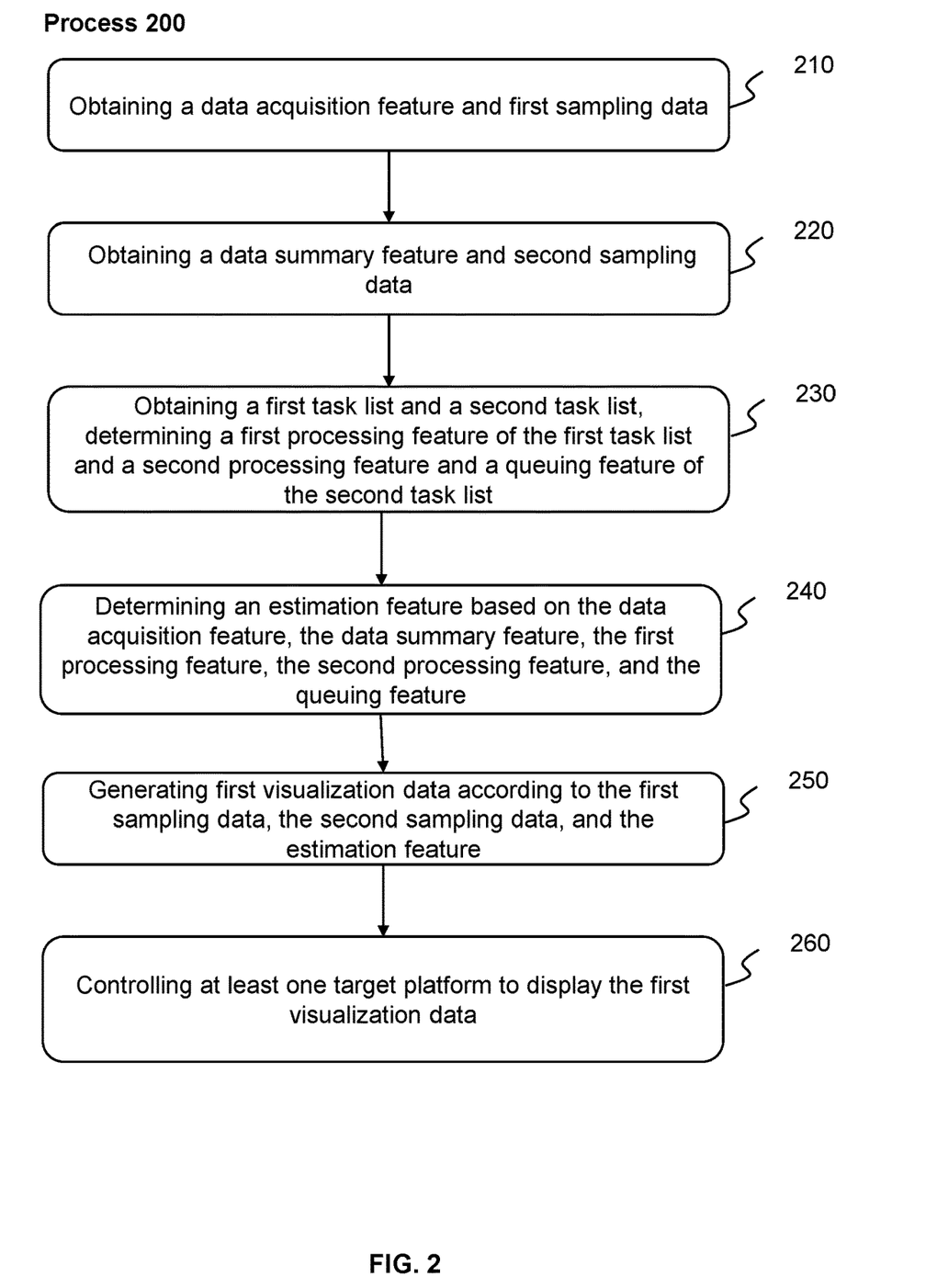
FIG. 2 is an exemplary flowchart of a method for visual management of smart gas data center processes according to some embodiments of the present disclosure.

FIG. 2 is an exemplary flowchart of a method for visual management of smart gas data center processes according to some embodiments of the present disclosure. In some embodiments, process 200 may be performed based on a smart gas management platform. As shown in FIG. 2, the process 200 includes the following steps.

Step 210, obtaining a data acquisition feature and first sampling data.

The data acquisition feature refers to a feature related to gas data acquisition, such as a type of gas data, an acquisition frequency, an acquisition accuracy, or the like. In some embodiments, gas data may be various data generated in the operation and management of the gas pipeline network, including but not limited to gas device data, gas usage data, and gas work order processing data. In some embodiments, the gas data may be obtained through monitoring by a smart gas object platform.

The first sampling data refers to data obtained by sampling the gas data.

In some embodiments, the smart gas management platform may obtain the data acquisition feature through preset or statistical means. For example, the smart gas management platform may obtain the data acquisition feature by counting the gas data acquired historically.

In some embodiments, the smart gas management platform may sample the gas data acquired by the smart gas object platform for a plurality of times to obtain the first sampling data. Due to the large amount of the gas data, processing the data one by one is time-consuming and duplicates the functions of the smart gas data center. Therefore, sampling of the acquired gas data is necessary. The smart gas management platform may randomly sample the gas data.

In some embodiments, a count of sampling times is related to an amount of data and a statistical probability of anomalies occurring in historically similar gas data. For example, the larger the amount of data and the greater the statistical probability of anomalies occurring in historical similar gas data, in order to ensure the accuracy of judgment, the amount of data that needs to be processed for gas data may be the larger, and the count of sampling times and the count of samples may be greater.

In some embodiments, the count of sampling times is related to an accumulation degree, which reflects the amount of abnormal data in the subsequent data. The more abnormal data there is, the greater the count of sampling times. Therefore, when the accumulation degree is large, the count of sampling times may be appropriately increased. For more information about the accumulation degree, refer to FIG. 5 and its associated description.

Step 220: obtaining a data summary feature and second sampling data.

The data summary feature refers to a feature of the gas data when it is summarized, such as a summary frequency, an amount of data, a data type, etc.

The second sampling data refers to data obtained by sampling the data summarized by a smart gas sensor network platform.

In some embodiments, the smart gas management platform may obtain the data summary feature through presets or statistics.

In some embodiments, the smart gas management platform may sample the gas data summarized by the smart gas sensor network platform to obtain the second sampling data. The process for obtaining the second sampling data is similar to the process for obtaining the first sampling data and may be determined based on the amount of data and/or the accumulation degree of the data. For details, please refer to the relevant descriptions above.

Step 230, obtaining a first task list and a second task list, determining a first processing feature of the first task list and a second processing feature and a queuing feature of the second task list.

The first task list refers to a gas task being processed. In some embodiments, the first task list includes at least one gas task.

The gas task refers to a task that processes gas data. For example, the gas task may include tasks such as gas data acquisition, gas data summary, and gas data analysis.

In some embodiments, the smart gas management platform may determine the first task list based on interaction information between the smart gas data center and other platforms. For example, the smart gas data center may determine the first task list from at least the smart gas sensor network platform, the smart gas object platform, the smart gas user platform, and the smart gas service platform, the smart gas data center may also determine the first task list from at least a gas business management sub-platform and a non-gas business management sub-platform. The first task list may include at least one type of a gas data summary task, a gas data acquisition task, and a gas data analysis task.

The first processing feature is a processing feature of each gas task in the first task list, such as a type of gas data being processed, an amount of processing, and a current processing status.

The second task list is a list of gas tasks that is not currently being processed. In some embodiments, the second task list includes at least one pending gas task.

In some embodiments, the smart gas management platform may determine the second task list based on information about the smart gas data center's interactions with other platforms. For example, the smart gas data center may determine the second task list from at least one of the smart gas sensor network platform, the smart gas object platform, the smart gas user platform, and the smart gas service platform, or form at least one of the gas business management sub-platform and the non-gas business management sub-platform. The second task list may include at least one type of a gas data summary task, a gas data acquisition task, or a gas data analysis task.

The second processing feature refers to a pending feature of each gas task in the second task list, such as a type of the pending gas data, an amount of processing, and so on.

The queuing feature refers to a queuing position of each gas task in the second task list. For example, the queuing feature may include a position of the gas task in the queue, etc.

In some embodiments, the smart gas management platform may determine the first processing feature based on the first task list, and determine the second processing feature and the queuing feature based on the second task list. For example, the smart gas management platform may perform statistics on the task information in the first task list and/or the second task list to determine the data type and an amount of processing corresponding to the gas task. The smart gas management platform may determine a queuing sequence of the gas task based on preset rules, and then determine the queuing feature of the gas task, among which the preset rules may be sorting based on task generation times, sorting based on task urgency degrees, etc.

Step 240, determining an estimation feature based on the data acquisition feature, the data summary feature, the first processing feature, the second processing feature, and the queuing feature.

The estimation feature refers to estimation information associated with the first task list and the second task list. In some embodiments, the estimation feature includes at least an estimated completion time for at least one gas task and an estimated queuing time of the at least one pending gas task.

The estimated completion time refers to an estimated processing completion time of the gas task being processed.

The estimated queuing time refers to an estimated waiting time for the pending gas task before processing.

In some embodiments, the smart gas management platform may pre-record and save a table that includes correlations between the data acquisition feature, the data summary feature, the first processing feature, the second processing feature, the queuing feature, the estimated completion time, and the estimated queuing time, and determine the estimation feature by looking up the table.

Figure 4:
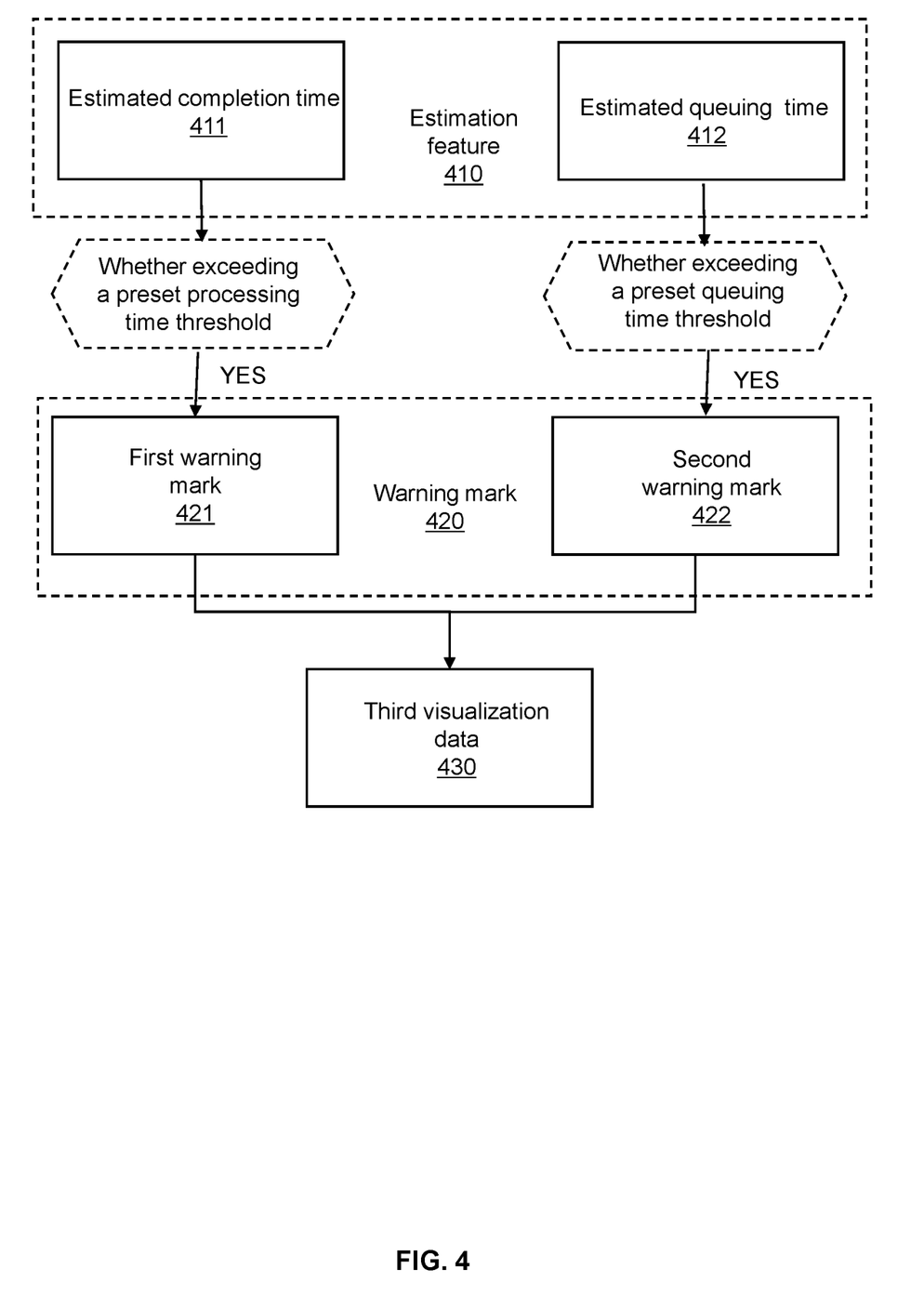
FIG. 4 is an exemplary flowchart for determining third visualization data according to some embodiments of the present disclosure.

In some embodiments, the smart gas management platform may also determine the estimated completion time and the estimated queuing time in other ways, as described in more detail in the relevant description in FIG. 4.

Step 250, generating first visualization data according to the first sampling data, the second sampling data, and the estimation feature.

The first visualization data refers to visualized information of the gas data. In some embodiments, the first visualization data may include an amount of the first sampling data and the second sampling data, a distribution of data types, a proportion of a current sampling volume accounting for a total amount of data, estimated features of each gas task at different stages, etc.

In some embodiments, the smart gas management platform may determine, based on the first sampling data, the second sampling data, and the estimation feature, the amount of data, the data type distribution, the proportion of the current sampling volume accounting for the total amount of data of the first sampling data and the second sampling data, and an estimation feature of each gas process, and aggregate them to generate the first visualization data based on a preset template of the first visualization data.

Step 260, controlling at least one target platform to display the first visualization data.

The target platform may include the smart gas object platform, the smart gas sensor network platform, the smart gas management platform, etc. Since different platforms focus on different data contents, the displayed focuses may differ among the platforms. For example, the first visualization data displayed by the smart gas object platform includes the visualization data of a plurality of devices on the object platform, such as parameters, a working status, an amount of acquired data, and a data upload frequency of each of the plurality of device. As another example, the first visualization data displayed by the smart gas sensor network platform includes the data transmission situation of the sensor network platform, such as the data load of different sub-platforms at different time periods, and the size of the data transmission amount. As another example, the first visualization data displayed by the smart gas management platform includes the data storage situation of the management platform, such as the storage situation (e.g., the storage load) of different databases of the smart gas data center.

In some embodiments, the smart gas management platform may generate a display instruction to control the display of the first visualization data by the at least one target platform. The display may include, but is not limited to, text, numbers, graphs, images, etc.

Figure 3:
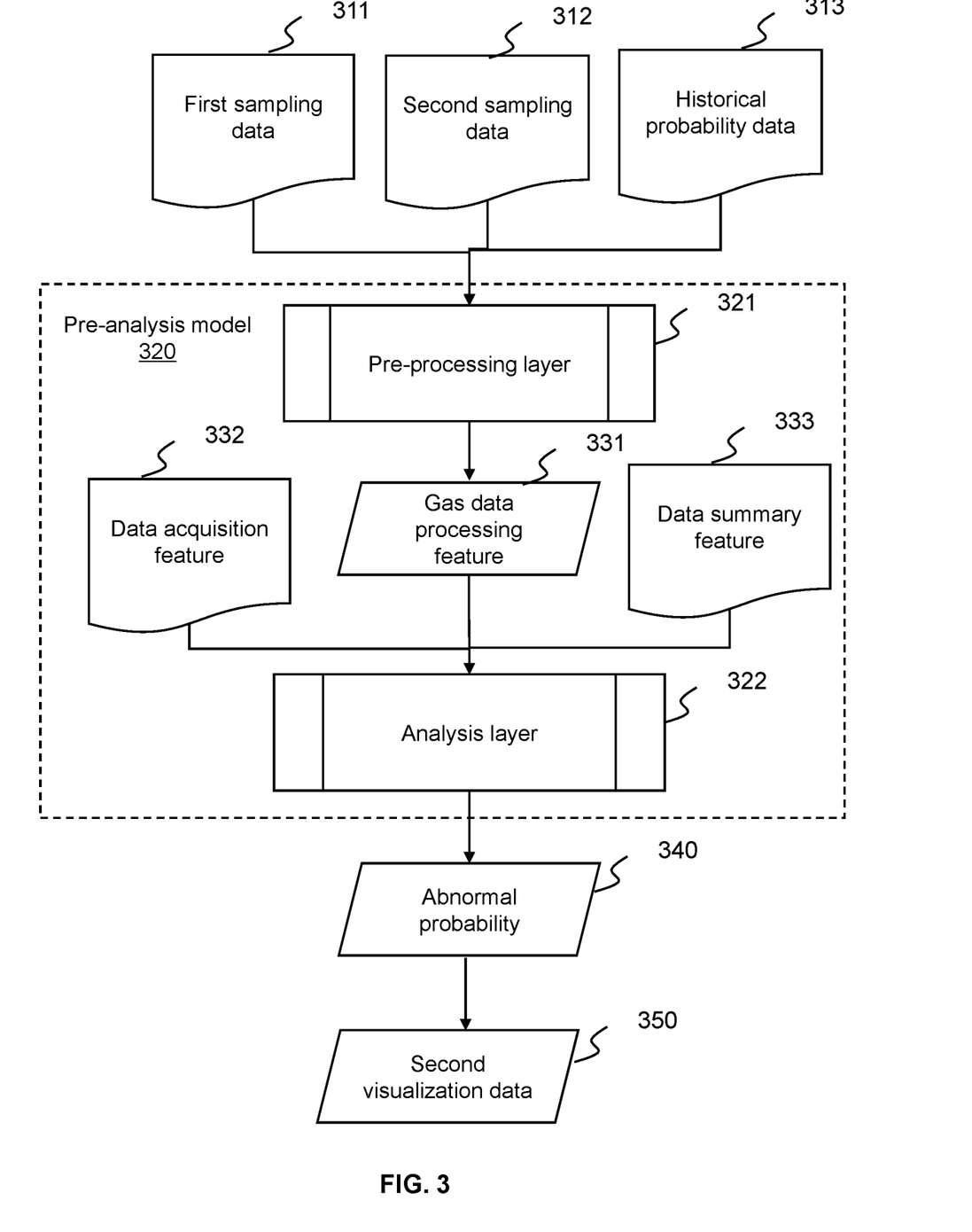
FIG. 3 is an exemplary schematic diagram of determining second visualization data according to some embodiments of the present disclosure.

In some embodiments, the smart gas management platform may also generate second visualization data based on the abnormal data and the abnormal probability, and display the second visualization data, as more may be seen in FIG. 3 and its related description.

In some embodiments, the smart gas management platform may also generate third visualization data based on a warning mark and display the third visualization data, as more may be seen in FIG. 4 and its related description.

In some embodiments of the present disclosure, the first visualization data is generated by using the first sampling data, the second sampling data, and the estimation feature. The at least one target platform is controlled to display the first visualization data, which is helpful for managing visualization information of gas processes on different sub-platforms.

It should be noted that the foregoing description of the process is for the purpose of exemplification and illustration only and does not limit the scope of the present disclosure. For a person skilled in the art, various corrections and changes may be made to the process under the guidance of the present disclosure. However, these corrections and changes remain within the scope of the present disclosure.

FIG. 3 is an exemplary schematic diagram of determining second visualization data according to some embodiments of the present disclosure.

In some embodiments, a smart gas management platform may determine abnormal data and an abnormal probability 340 corresponding to the abnormal data based on first sampling data 311, second sampling data 312, a data acquisition feature 332, and a data summary feature 333; generate second visualization data 350 based on the abnormal probability 340 corresponding to the abnormal data, and control at least one target platform to display second visualization data 350.

For more information on the first sampling data, second sampling data, data acquisition feature, and data summary feature, please refer to the description in FIG. 2.

The abnormal data refers to data that may have anomalies. By way of example only, the abnormal data may include, but is not limited to, the data source itself and abnormal sampling data during network transmission or data processing. For example, the abnormal data may include sampling data with an abnormal data value or an abnormal amount of data. As another example, the abnormal data may also include sampling data for which the transmission process may have packet loss issues. As another example, the abnormal data may also include sampling data where the data distribution may be unreasonable. Unreasonable means not conforming to normal patterns, for example, deviation from the mean of the sampling data by more than twice the standard deviation, and so on.

The abnormal probability is a probability that a data abnormal occurs in the data. The higher the abnormal probability, the higher the likelihood that the abnormal data is suspicious data.

The smart gas management platform may determine the abnormal data and the abnormal probability corresponding to the abnormal data based on the first sampling data, the second sampling data, the data acquisition feature, and the data summary feature in multiple ways.

In some embodiments, the smart gas management platform may use an outlier monitoring algorithm to analyze and process the first sampling data, the second sampling data, the data acquisition feature, and the data summary feature to determine whether there is abnormal data and the abnormal probability corresponding to the abnormal data. Exemplarily, the outlier monitoring algorithm may include but is not limited to, a K Nearest Neighbor (KNN) algorithm, One-Class SVM, or the like.

In some embodiments, the smart gas management platform may determine the abnormal probability 340 corresponding to the abnormal data through a pre-analysis model 320 based on the first sampling data 311, the second sampling data 312, the data acquisition feature 332, and the data summary feature 333.

The pre-analysis model 320 may be used to determine the abnormal data and the abnormal probability corresponding to the abnormal data. In some embodiments, the pre-analysis model may be a machine learning model with a custom structure as described below. The pre-analysis model may also be a machine learning model of another structure, e.g., a neural network model, etc.

In some embodiments, an input of the pre-analysis model 320 may include the first sampling data 311, the second sampling data 312, the data acquisition feature 332, and the data summary feature 333, and an output may be the abnormal data and the abnormal probability 340 corresponding to the abnormal data.

In some embodiments, the pre-analysis model 320 includes a pre-processing layer 321 and an analysis layer 322.

The pre-processing layer 321 may be a machine learning model such as a recurrent neural network model.

In some embodiments, an input of the pre-processing layer 321 may include the first sampling data 311, the second sampling data 312, historical probability data 313, and ab output may include a gas data processing feature 331.

The historical probability data 313 may be data reflecting possible anomalies in historical gas processing data and a historical abnormal probability. For example, the historical probability data 313 may include historical abnormal data and its corresponding historical abnormal probability among a plurality of sets of identical or similar historical gas treatment data, wherein the historical abnormal data and its corresponding historical abnormal probability may be determined by analyzing the historical data by the smart gas management platform.

The plurality of sets of identical or similar historical gas treatment data may be determined by calculating a vector distance between the historical first sampling data and the first sampling data, or a vector distance between the historical second sampling data and the second sampling data.

The gas data processing feature 331 may be used to reflect features of abnormal data. For example, the gas data processing feature 331 may include preliminary screening results for possible anomalies in the sampling data. As another example, the gas data processing feature 331 may include a maximum value, a minimum value, etc., in the sampling data. The sampling data may include at least one of the first sampling data and the second sampling data.

In some embodiments, the gas data processing feature may include a labeled portion of the first sampling data and/or the second sampling data, and a corresponding label. Among them, the labeled portion includes data that is judged to be abnormal in the first sampling data and/or the second sampling data, and the corresponding probability is a probability of anomalies in the aforementioned data.

The analysis layer 322 may be a machine learning model, such as a neural network model.

In some embodiments, an input of the analysis layer 322 may include the gas data processing feature 331, the data acquisition feature 332, and the data summary feature 333, and an output may include at least one set of abnormal data and the abnormal probability 340 corresponding to the abnormal data.

In some embodiments, the pre-analysis model may be obtained by joint training based on a large number of first training samples with first labels. The first training samples for joint training include at least one set of sample first sampling data, sample second sampling data, a sample data acquisition feature, and a sample data summary feature. The first label may include at least one set of data corresponding to the first training sample that has an abnormal. The first training sample may be obtained based on historical data. The first label may be obtained based on manual or automatic labeling. For example, the first label may be determined based on the historical gas treatment data whether there is an abnormal, and if there is an abnormal in a certain set of historical gas treatment data, the first label is 1, otherwise it is 0.

An exemplary joint training process is as follows: inputting the sample first sampling data and the sample second sampling data in the first training sample into an initial pre-processing layer, obtaining an initial gas data processing feature output from the initial data processing layer, inputting the output of the initial pre-processing layer, the sample data acquisition feature, and the sample data summary feature into an initial analysis layer, and obtaining at least one set of initial abnormal data and an abnormal probability corresponding to the initial abnormal data; constructing a loss function based on the output of the initial analysis layer and the first label, and updating parameters of the initial pre-processing layer and the initial analysis layer until preset conditions are satisfied and the training is completed. The preset conditions may include the loss function being less than a threshold, convergence, or the training period reaching a threshold.

In some embodiments of the present disclosure, efficiency of data processing can be further improved and the accuracy of predicting abnormal data can be enhanced by setting the pre-analysis model as the pre-processing layer and the analysis layer and processing the corresponding data separately in the different layers. By using the trained pre-analysis model, the abnormal data and the abnormal probability corresponding to the abnormal data can be determined relatively quickly before or during the formal processing of the gas data, thus generating visualization and management information for other platforms to provide timely feedback on abnormal data of their interest.

The second visualization data refers to visual presentation of the features of the abnormal data. For example, the second visualization data may include the presence of abnormal data, the type of abnormal data, a ratio of the amount of abnormal data to the amount of sampling data, and so on. The type of abnormal data may be a possible type of abnormal that the abnormal data may have. For example, the type of abnormal data may include missing data, data that is too large or too small, data with high variability, data with poor authenticity, or the like.

The smart gas management platform may generate the second visualization data based on the abnormal data and the abnormal probability in multiple ways. In some embodiments, the smart gas management platform may identify and analyze the abnormal data in the first sampling data and/or the second sampling data by determining the type of abnormal data, the amount of abnormal data, and calculating the ratio of the amount of abnormal data to the amount of sampling data. In some embodiments, the smart gas management platform may generate the second visualization data based on the aforementioned type of abnormal data, the amount of abnormal data, and the ratio of the amount of abnormal data to the amount of sampling data and combined with a preset template of the second visualization data.

In some embodiments, the second visualization data may also be associated with a platform perception degree.

The platform perception degree refers to a degree of demand for different types of abnormal data by different target platforms. For example, the smart gas data center may prefer to send the second visualization data to a more demanding target platform. In some embodiments, the platform perception degree of at least one target platform may be determined based on the type of data processed by the platforms themselves.

In some embodiments, there is a difference in the degree of demand for different types of abnormal data by different target platforms. Therefore, for different types of abnormal data, the smart gas data center sends the corresponding second visualization data to different target platforms.

For example, the smart gas object platform is used for all types of gas data, so the smart gas object platform has a higher platform perception degree with possible abnormalities in the data itself. If the data itself is suspicious, the smart gas data center may push the second visualization data to the smart gas object platform to prompt relevant personnel to further confirm whether there are issues such as aging or failure in the acquisition devices in the smart gas object platform.

Another example is that the smart gas service platform aggregates feedback information from the smart gas user platform. The feedback information may include abnormalities in the gas pipeline network device or abnormalities in gas usage. Therefore, the smart gas service platform has a higher platform perception degree with the abnormal data values. If there is suspicious data with abnormal data values, it may involve work order repairs or confirming whether there is an issue with the corresponding gas user. Therefore, the second visualization data needs to be sent to the smart gas service platform.

Another example is that the smart gas sensor network platform is used to summarize and transmit various types of data. Therefore, the smart gas sensor network platform has a higher platform perception degree with abnormal amount of data. If there is suspicious data with abnormal amount of data, the second visualization data may be sent to the smart gas sensor network platform. Therefore, it is necessary to determine whether the sensor network platform has anomalies in data summary and other aspects.

In some embodiments of the present disclosure, different platform perception degrees correspond to different second visualization data, which is conducive to the targeted sending of visualization data to different sub-platforms and improving the accuracy of displaying visualization data related to gas processing.

In some embodiments, the smart gas management platform may predict the abnormal data in the gas data and determine the abnormal probability, generate the second visualization data, and send it to at least one sub-platform of the subsequent data processing process for visualization display. Different sub-platforms display different objects. For example, second visualization data of a gas operation service sub-platform may be displayed to gas staff corresponding to the gas operation service sub-platform, and second visualization data of a user sub-platform may be displayed to a gas user corresponding to the user sub-platform. The display manner may be different, and the second visualization data may include the abnormal probability.

For example, if the work order dispatch sub-platform receives the second visualization data from the gas data center, and the second visualization data indicates a 90% probability of abnormal data in a certain area, the work order executives in that area are notified to be prepared in advance.

Another example is when a user consults through the call center management platform, the gas data center analyzes the user's gas data, predicts potential issues in the user's gas device, and then sends the second visualization data promptly to remind the user.

In some embodiments of the present disclosure, by visualizing the second visualization data, the staff can evaluate the processing results of the gas data center in advance and make arrangements instead of waiting for the complete analysis and processing of all the data, thereby improving processing efficiency.

FIG. 4 is an exemplary flowchart for determining third visualization data according to some embodiments of the present disclosure.

In some embodiments, the smart gas management platform may determine a warning mark 420 based on an estimation feature 410; generate third visualization data 430 based on the warning mark 420; and control at least one target platform to display the third visualization data 430.

The estimation feature 410 may include an estimated completion time 411 and an estimated queuing time 412, and more details about the estimation feature may be found in the related description of FIG. 2.

The warning mark refers to a mark used to indicate a timeout.

In some embodiments, the warning mark 420 may include a first warning mark 421, a second warning mark 422, or the like. The first warning mark 421 is used to prompt the timeout of gas task processing time, and the second warning mark 422 is used to prompt the timeout of gas task queue time.

The warning mark may be obtained in various ways. For example, the smart gas management platform may determine whether an estimated completion time and/or an estimated queuing time of the sampling data exceed a preset time threshold, and if so, the warning mark is issued. The preset time threshold may be a threshold condition related to time. For example, the preset time threshold may include a preset processing time threshold and a preset queuing time threshold. The preset processing time threshold and the preset queuing time threshold may be determined based on experience or experimentation.

The first warning mark is a mark related to the processing time of the gas data. For example, the first warning mark may include a mark for a gas task processing timeout.

In some embodiments, the smart gas management platform may determine the first warning mark based on the estimated completion time.

For more information on the estimated completion time, refer to the related description in FIG. 2.

In some embodiments, the smart gas management platform may determine the estimated completion time based on a preset algorithm. The preset algorithm may be a formula or mapping relationship, etc.

For example, the preset algorithm may be:

$$T = t_0 \times A + \sum_{i=1}^{n} B_i \times P_i \times A$$

In the formula, the estimated completion time is T, and a standard time range for data processing is $t_0$. A is a weighting coefficient, which may be related to the amount of sampling data. The larger the amount of sampling data, the larger the value of A. n is a count of types of abnormal data. $P_i$ represents the probability that the data is of the ith class abnormal data, while $B_i$ represents an average processing time for the ith class abnormal data. The value of $B_i$ may be determined based on the historical average processing time for the corresponding historical abnormal data types. It should be noted that different types of historical abnormal data correspond to different historical average processing times.

For different regions, the gas data center has different processing times for gas repair data, gas maintenance data, and gas inspection data. As a result, there are differences in the standard time range $t_0$ for data processing in different regions.

For gas flow statistic data (which may be used as the basis for future gas peak pressure regulation) at different times, the gas data center also needs to consider the importance of different gas users or different gas branch pipelines to determine the processing time of the data. Therefore, there are differences in the standard time range $t_0$ for data processing at different times.

In some embodiments, the smart gas management platform may determine whether the estimated completion time exceeds a preset processing time threshold, and if so, the first warning mark is issued.

The second warning mark is related to the queuing time of the gas data. For example, the second warning mark may include a queuing timeout mark.

In some embodiments, the smart gas management platform may determine the second warning mark based on the estimated queuing time.

For more information on the estimated queuing time, please refer to the relevant description in FIG. 2.

In some embodiments, for each set of sampling data, the smart gas management platform determines, based on the queuing information of the set of sampling data, at least one piece of preceding data queued in front of any of the data, calculates a total completion time of the at least one piece of preceding data based on the estimated completion time of each piece of preceding data, and then determines the estimated queuing time for the sampling data based on the total completion time mentioned above.

In some embodiments, the smart gas management platform checks whether the estimated queuing time exceeds a preset queuing time threshold. If so, the second warning mark is set.

In some embodiments of the present disclosure, by considering the type of the abnormal data and the abnormal probability, the estimated completion time can be determined in a manner that is more consistent with reality, improving the accuracy of the first warning mark. This not only enhances the reliability of determining the estimated queuing time but also improves the accuracy of the second warning mark.

In some embodiments, the smart gas management platform determines an accumulation degree of at least one target platform based on a data flow graph; and determines the warning mark based on the accumulation degree and the estimation feature. For more details regarding this embodiment, please refer to the relevant description in FIG. 5.

The third visualization data presents visual representation of the estimated processing time and the estimated queuing time for each set of sampling data.

The third visualization data may be generated in multiple ways based on the warning mark. In some embodiments, the smart gas management platform sets the first warning mark for the first sampling data that exceeds the processing timeout and the second warning mark for the second sampling data that exceeds the queuing timeout. Then, it generates the third visualization data based on both the first warning mark and the second warning mark. The third visualization data may include, but is not limited to, text, numbers, icons, and images.

In some embodiments, the third visualization data may be displayed only on the gas data center. For example, the third visualization data may include a visual presentation of processing timeouts for data between different sub-platforms within the gas data center. For example, the third visualization data may include a visualization of a timeout for sending data from the gas data center to other sub-platforms within the smart gas management platform.

In some embodiments of the present disclosure, in the process of processing data in the gas data center, a possible timeout situation is determined based on the estimation feature, and the warning mark in the form of a visualization is timely carried out, so that the other sub-platforms can be informed in advance of the data processing process situation and make timely preparations.

Figure 5:
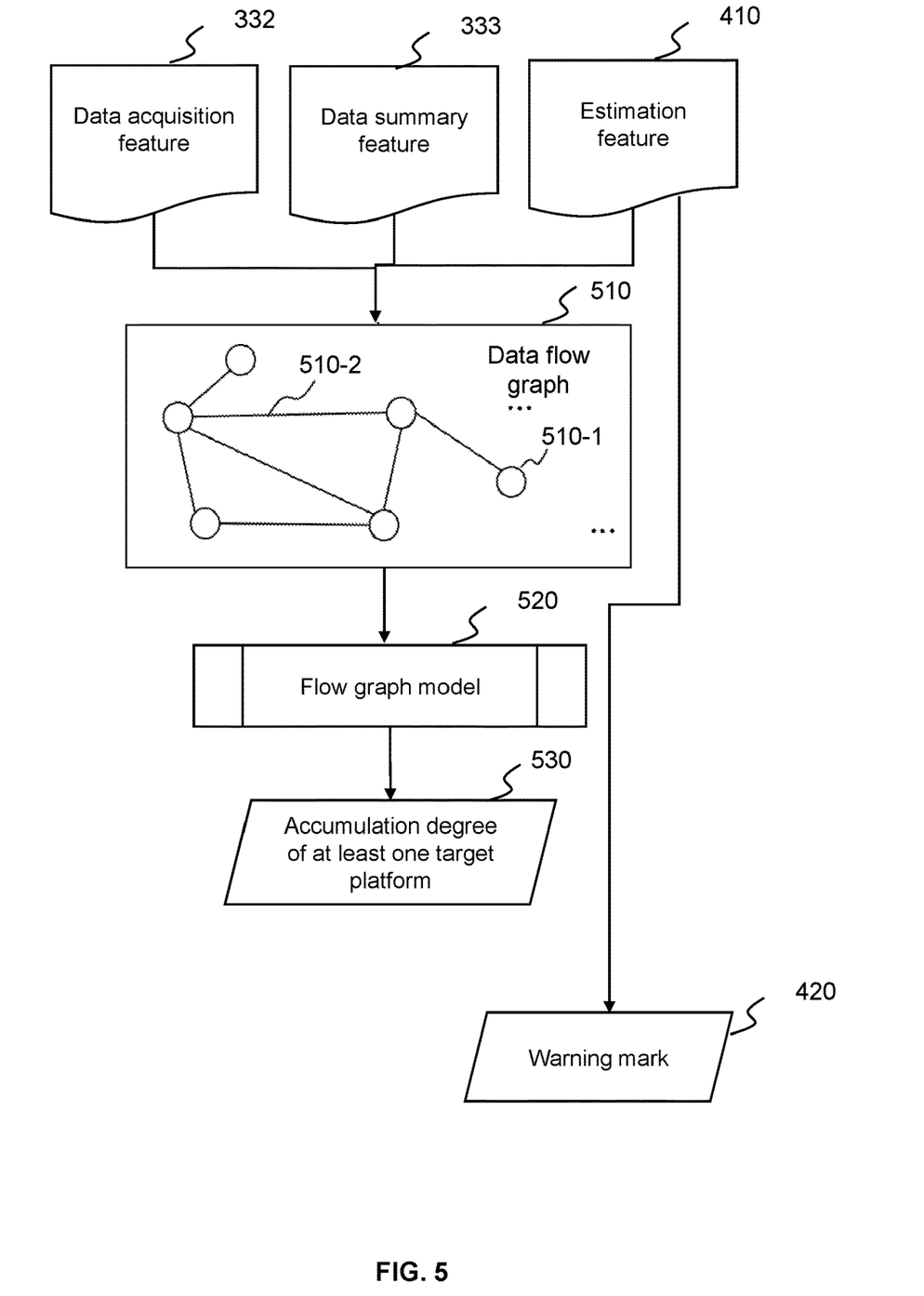
FIG. 5 is an exemplary flowchart for determining a warning mark according to some embodiments of the present disclosure.

FIG. 5 is an exemplary flowchart for determining a warning mark according to some embodiments of the present disclosure.

In some embodiments, a smart gas management platform may generate a data flow graph 510 based on the data acquisition feature 332, the data summary feature 333, and the estimation feature 410, the data flow graph 510 includes at least one node 510-1 and at least one edge 510-2, the at least one node 510-1 representing at least one target platform, and the at least one edge 510-2 representing a data flow feature between any two nodes.

The data flow graph may be used to characterize a transmission relationship of the gas data between platforms. In some embodiments, the data flow graph may be a data structure including nodes and edges, with the edges connecting the nodes, and the nodes and edges may have features.

The nodes correspond to at least one target platform. The node features may reflect information related to the target platform. For example, the node features may include a platform type of a target platform, an accumulation degree, or the like. Detailed descriptions of the target platform may be found in the related description in FIG. 2.

The accumulation degree may reflect the accumulation degree of unprocessed abnormal data. The greater the accumulation degree, the more unprocessed abnormal data there is.

In some embodiments, the accumulation degree may also be positively correlated with an estimated processing time and an estimated queuing time. The longer the estimated processing time and the estimated queuing time, the greater the accumulation degree.

The edges may correspond to data transmission relationships, for example, two target platforms that have a data transmission relationship have an edge between them, and the direction of data transmission follows the direction of the edge. The edge features may reflect information about the data transfer. For example, the edge features may include the data flow feature, or the like.

The data flow feature may characterize the data acquisition feature, the data summary feature, the estimation feature, and predictive data queuing information for the at least one set of the gas data. The at least one set of gas data refers to data that needs to be transmitted or is being transmitted at a certain point in time.

It should be noted that the predictive data queuing information is different from the aforementioned queuing information of the sampling data. The predictive data queuing information may represent the queuing information of the gas data in two nodes that are connected by an edge and is waiting to be transmitted to the data receiving platform in the data sending platform. The data sending platform refers to a platform in the at least one target platform that performs data sending, and the data receiving platform refers to a platform in the at least one target platform that performs data receiving. For further description of the at least one target platform, please refer to the relevant description in FIG. 2 of the present disclosure.

In some embodiments, the predictive data queuing information may include predictive data queuing information for the target platform at a current moment, predictive data queuing information for a future moment, or the like. The predictive data queuing information at the current moment refers to a queuing order of the gas data that is waiting to be transmitted at the current moment. The predictive data queuing information for the current moment may be obtained by querying.

The queuing order of the gas data that may need to be transmitted at a future moment is referred to as the predictive data queuing information for the future moment. The predictive data queuing information for the future moment may be predicted based on modeling or by using various data analysis algorithms, such as timing analysis algorithms, etc., to analyze and process the gas data from different nodes.

In some embodiments, the edges have directions, and the nodes may have outgoing and/or incoming edges. Incoming edges refer to edges that point to a node, while outgoing edges are edges that start from a node and point to another node. In other words, the target platform may transmit data to other target platform and may receive data transmitted by other target platform.

In some embodiments, the data flow feature also includes a data urgency degree.

The data urgency degree may indicate a level of urgency for the gas data processing task. For example, the data urgency degree may be represented by a number, where a larger value indicates a higher level of urgency for the data processing task. In some embodiments, the corresponding data urgency degree may be pre-set based on the type of the gas data, relying on actual experience.

In some embodiments of the present disclosure, the processing of the gas data not only needs to consider the existence of abnormal data and the amount of abnormal data but also needs to consider the urgency degree of the gas data to make the analysis and visualization of the abnormal data more in line with actual needs.

The accumulation degree of the target platform may be determined in various ways. In some embodiments, the smart gas management platform may obtain a historical data flow graph that is the same or similar to the data flow graph based on the data flow graph, and determine the accumulation degree of the target platform by obtaining an accumulation degree of different nodes of the historical data flow graph after a preset time period. The preset time period may be determined based on a time interval between the future moment to be predicted and the current moment. For example, based on the feature vectors composed of the node features and the edge features of the data flow graph, and by calculating vector distances between the feature vectors and the historical feature vectors, a historical data flow graph corresponding to a historical feature vector with the smallest vector distance is determined as the historical data flow graph same or similar to the data flow graph.

In some embodiments, the smart gas management platform may determine an accumulation degree of the at least one target platform 530 based on the data flow graph 510 via a flow graph model 520.

The flow graph model may be used to predict the accumulation degree of the at least one target platform. The flow graph model may be a graph neural network (GNN) model or other graph models, such as a graph convolutional neural network (GCNN) model. The flow graph model may also be constructed by adding other processing layers in the graph neural network model or modifying processing methods.

In some embodiments, an input of the flow graph model may include the data flow graph 510, and an output of the flow graph model may include the accumulation degree of at least one target platform.

In some embodiments, the flow graph model may be trained based on training data. The training data includes a second training sample and a second label. For example, the second training sample may include sample data flow graph for at least one historical moment, and the second label may be an accumulation degree of at least one target platform in the sample data flow graph. The nodes and their attributes in the sample data flow graph, as well as the edges and their attributes, are similar to the above description. The second training sample may be determined based on historical data, and the second label is determined by manual labeling. The sample moment refers to a historical time point.

In some embodiments described in the present disclosure, prediction of the accumulation degree of different nodes at future time points can be achieved through data flow graph and the use of the flow graph model based on complex physical intrinsic connections, which is beneficial for determining the reliability of the warning mark and efficiently conserving resources.

In some embodiments, when the accumulation degree of the at least one target platform is greater than an accumulation threshold, the smart gas management platform may adjust the processing order of at least one pending gas task and reuse the flow graph model based on the adjusted processing order for analysis until the accumulation degree meets a preset condition.

The accumulation threshold may be a threshold condition related to the accumulation degree. The accumulation threshold may be a value determined based on experience or experimentation.

The preset condition may be a criterion used to evaluate whether to adjust the processing order of the pending gas task. For example, the preset condition may include at least one target platform whose the accumulation degree is less than the accumulation threshold.

In some embodiments, the smart gas management platform may adjust the order in the gas treatment process of pending gas data in response to the accumulation degree of at least one node is greater than the preset accumulation threshold.

Adjusting the order in the gas processing flow of the pending gas data can include adjusting the edge features associated with a target node, such as adjusting a queuing order of the gas data in the data flow feature. The target nodes may be nodes corresponding to a platform whose accumulation degree is greater than the preset accumulation threshold.

In some embodiments, the smart gas management platform may reconstruct the data flow graph based on adjusting the processing order of at least one pending gas task to be re-predicted by the flow graph model until the accumulation degrees of predicted future moments of all the nodes satisfy the preset condition.

In some embodiments of the present disclosure, the efficiency of the gas data processing can be improved by adjusting the processing order of at least one pending gas task, and the processing schedule of the gas data that is not currently required to be processed can be postponed, which can reduce resource waste and alleviate the pressure on data processing.

In some embodiments, the smart gas management platform may determine the warning mark in multiple ways based on the accumulation degree and the estimation feature 410 of the at least one target platform at a future moment. For example, the smart gas management platform may determine the warning mark based on modeling or using various data analysis algorithms, such as regression analysis, to analyze and process the accumulation degree of the at least one target platform and the estimation feature.

In some embodiments of the present disclosure, the data flow graph is constructed based on relevant gas data, taking into account the urgency of the data. By using the trained flow graph model, the accumulation degree of different platforms can be better predicted. Based on the accumulation degree, it can be determined whether to adjust the order of data analysis and processing to meet the data processing requirements.

One or more embodiments of the present disclosure further provide a non-transitory computer-readable storage medium storing computer instructions, wherein when reading the computer instructions, a computer executes the method for visual management of smart gas data center processes as described in any of the above embodiments.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Furthermore, the particular features, structures, or characteristics may be combined as suitable in one or more embodiments of the present disclosure.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

What is claimed is:
1. A method for visual management of smart gas data center processes, wherein the method is executed by a smart gas management platform of an Internet of Things system for visual management of smart gas data center processes, comprising:

obtaining a data acquisition feature and first sampling data;

obtaining a data summary feature and second sampling data;

obtaining a first task list and a second task list, determining a first processing feature of the first task list and a second processing feature and a queuing feature of the second task list; wherein
the first task list includes at least one gas task, and the second task list includes at least one pending gas task;

determining an estimation feature based on the data acquisition feature, the data summary feature, the first processing feature, the second processing feature, and the queuing feature, the estimation feature at least including an estimated completion time of the at least one gas task, and an estimated queuing time of the at least one pending gas task;

generating first visualization data according to the first sampling data, the second sampling data, and the estimation feature;

controlling at least one target platform to display the first visualization data;

determining abnormal data and an abnormal probability corresponding to the abnormal data according to the first sampling data, the second sampling data, the data acquisition feature, and the data summary feature;

generating second visualization data based on the abnormal data and the abnormal probability;

controlling the at least one target platform to display the second visualization data;

determining a warning mark according to the estimation feature;

generating third visualization data according to the warning mark; and controlling the at least one target platform to display the third visualization data.

2. The method according to claim 1, wherein the determining a warning mark according to the estimation feature includes:

generating a data flow graph based on the data acquisition feature, the data summary feature, and the estimation feature, the data flow graph including at least one node and at least one edge, the at least one node representing the at least one target platform, and the at least one edge representing a data flow feature between any two nodes;

determining an accumulation degree of the at least one target platform based on the data flow graph; and determining the warning mark based on the accumulation degree and the estimated feature.

3. A non-transitory computer-readable storage medium storing computer instructions, wherein when reading the computer instructions, a computer executes a method for visual management of smart gas data center processes, the method comprising:

obtaining a data acquisition feature and first sampling data;

obtaining a data summary feature and second sampling data;

obtaining a first task list and a second task list, determining a first processing feature of the first task list and a second processing feature and a queuing feature of the second task list; wherein
the first task list includes at least one gas task, and the second task list includes at least one pending gas task;

determining an estimation feature based on the data acquisition feature, the data summary feature, the first processing feature, the second processing feature, and the queuing feature, the estimation feature at least including an estimated completion time of the at least one gas task, and an estimated queuing time of the at least one pending gas task;

generating first visualization data according to the first sampling data, the second sampling data, and the estimation feature;

controlling at least one target platform to display the first visualization data;

determining abnormal data and an abnormal probability corresponding to the abnormal data according to the first sampling data, the second sampling data, the data acquisition feature, and the data summary feature;

generating second visualization data based on the abnormal data and the abnormal probability;

controlling the at least one target platform to display the second visualization data;

determining a warning mark according to the estimation feature;

generating third visualization data according to the warning mark; and controlling the at least one target platform to display the third visualization data.

\* \* \* \* \*